(12) United States Patent
Yoshida et al.

(10) Patent No.: US 7,875,301 B2
(45) Date of Patent: Jan. 25, 2011

(54) AGENT FOR INCREASING GRANULOCYTE MACROPHAGE COLONY STIMULATING FACTOR

(75) Inventors: Satoshi Yoshida, Tokyo (JP); Takahisa Ushiroyama, Takatsuki (JP)

(73) Assignee: Original Image Co., Ltd., Yokohama-Shi (JP)

( * ) Notice: Subject to any disclaimer, the term of this patent is extended or adjusted under 35 U.S.C. 154(b) by 802 days.

(21) Appl. No.: 10/553,798

(22) PCT Filed: Apr. 16, 2004

(86) PCT No.: PCT/JP2004/005444

§ 371 (c)(1), (2), (4) Date: Oct. 18, 2005

(87) PCT Pub. No.: WO2004/091643

PCT Pub. Date: Oct. 28, 2004

(65) Prior Publication Data

US 2006/0127507 A1 Jun. 15, 2006

(30) Foreign Application Priority Data

Apr. 18, 2003 (JP) .............................. 2003-115109

(51) Int. Cl.
*A61K 36/68* (2006.01)
*A61K 36/28* (2006.01)
*A61K 36/355* (2006.01)

(52) U.S. Cl. ....................... 424/758; 424/738; 424/764; 514/814

(58) Field of Classification Search ........................ None
See application file for complete search history.

(56) References Cited

U.S. PATENT DOCUMENTS

| | | | |
|---|---|---|---|
| 4,421,746 A | 12/1983 | Kojima et al. | |
| 4,456,597 A | 6/1984 | Kojima et al. | |
| 4,469,685 A | 9/1984 | Kojima et al. | |
| 5,753,266 A | 5/1998 | Youssefyeh et al. | |
| 5,882,672 A | 3/1999 | Kojima et al. | |

FOREIGN PATENT DOCUMENTS

| | | |
|---|---|---|
| JP | 2813471 B | 8/1998 |
| JP | 10-279491 | 10/1998 |
| JP | 11-116498 | 4/1999 |
| JP | 2000-281584 | 10/2000 |

OTHER PUBLICATIONS

Nissen et al., Failure of Recombinant Human Granulocyte-Macrophage Colony-Stimulating Factor Therapy in Aplastic Anemia Patients with Very Severe Neutropenia, 1988, Blood, vol. 72: 2045-2047.*
Tropilab http://www.tropilab.com/cucur-max.html.*
Unigraz http://www.uni-graz.at/~katzer/engl/Cart_tin.html.*
Herbalremedies http://www.herbalremedies.com/psylliumhusk.html.*
USDA http://plants.usda.gov/java/profile?symbol=LOJA.*
Weisbart et al., Huamn granulocyte-macrophage colony-stimulating factor is a neutrophil activator, 1985, Nature, 314, 361-363.*
Levine et al., Daily subcutaneous recombinant granulocyte-macrophage colony stimulating factor improves the neutropenia induced by azidothymidine in patients with AIDS/ARC; follow up, 1989, Int Conf AIDS, 5, 406.*
Falange et al., Neutrophil Activation and Hemostatic Changes in Healthy Donors Receiving Granulocyte Colony-Stimulating Factor, 1999, Blood, 93, 2506-2514.*
Mar. 24, 2009 tropilab http://www.tropilab.com/cucur-max.html.*
Mar. 24, 2009 Unigraz http://www.uni-graz.at/~katzer/engl/Cart_tin.html.*
Mar. 24, 2009 Herbalremedies http://www.herbalremedies.cim/psylliumhusk.html.*
Mar. 24, 2009 USDA http://plants.usda.gov/java/profile?symbol=LOJA.*
Baert, F.J. et al., "Tumor Necrosis Factor α-antibody (Infliximab) Therapy Profoundly Down-Regulates the Inflammation in Crohn's Disease," Gastroenterology (1999) vol. 116, pp. 22-28.
Ehrenpreis, E.D. et al., "Thalidomide Therapy for Patients with Refractory Crohn's Disease: An Open-Label Trial," Gastroenterology (1997), vol. 117, pp. 1271-1277.
The Merck Manual 16th Edition, p. 1240, 1994.
Mizoguchi, M., "GM-CSF" in Cytokine Therapy: Approach From Basis and Pathema, (1993) Nankodo Co., Ltd., Tokyo p. 39-45, ISBN: 4524233628.
Nicola, N.A., "GM-CSF" in Cytokine Reference a Compendium of Cytokines and Other Mediators of Host Defense, Oppenheim & Feldman, eds., (2001) Academic Press, pp. 899-910.
Takeuchi, T., "Anti-TNF α Therapy" in Separate Volume: Progress of Medical Science, Immunodeficiency, (2002) Ishiyakushuppan Co., Ltd., pp. 538-542.
Urabe, A., "Blood Disease and Cytokine Therapy, Cytokine Therapy Approach from Start and Pathema," (1993) Nankodo Co., Ltd., Tokyo, pp. 184-194.
Watanabe, N., "Development of Highly Sensitive Assay for Detection of Intravital Trace Materials and Its Clinical Application," Lab. Clin. Pract. (2002), vol. 20(2), pp. 110-114.
Yamamura, M., "Clinical Analysis and Treatment of Anemia in Patients of Rheumatoid Arthritis," Report for 6th Incentive Award of the Society of Certifying Specialist in Internal Medicine, 1998.
Atoyama, et al., "Heikeigo Futei Shusorei ni Okeru Macrophage Activating Chinese Mixed Herbs (MACH) no Men'ekikei Inshi Chosei Sayo to Rinsho Koka", Japanese Journal of Oriental medicine, vol. 54, pp. S118 and S247, (Apr. 2003).

(Continued)

*Primary Examiner*—Michele Flood
*Assistant Examiner*—Catheryne Chen
(74) *Attorney, Agent, or Firm*—Finnegan, Henderson, Farabow, Garrett & Dunner LLP

(57) ABSTRACT

The provision of a GM-CSF increasing agent or a TNF-α modulator, which is a composition comprising *Cucurbita moschata, Carthamus tinctorius, Plantago asiatica* and *Lonicera japonica*; or a health food, nutritional supplementary food, or the like for increase of GM-CSF, and the prevention of Crohn's disease and the like, and the prognosis thereof, which comprises *Cucurbita moschata, Carthamus tinctorius, Plantago asiatica* and *Lonicera japonica*.

2 Claims, No Drawings

OTHER PUBLICATIONS

Yamamoto, et al., "Taka Shibosan ni yoru Seitai Hanno Shushoku", JJPEN, vol. 23, No. 6, Fig. 3, pp. 321-325, (2001).

Hayashi, et al., "Shinshuka ni Okeru n-3-Kei Shibo Nyuzai no Toyoryo ga Men'eki Hanno ni Ataeru Koka to Granulocyte-Macrophage Colony Stimulating Factor (GMCSF), no Kanyo", The Japanese Journal of Surgical Metabolism and Nutrition, vol. 31, No. 4, Fig. 3, pp. 225-233, (1997).

Skrzypczak, et al., "M GM-CSF Influence the ability to fertilize oocyte?", Ginekologia polska, vol. 70, No. 6, pp. 433-439, (1999).

Inukai, et al., "Benibanachu no Serotonin Yudotai no Enshosei Sansho Sogai Narabi ni Sen'l Ga Saibo Zoshoku Sayo", Symposium on Toxicology and Environmental Health, vol. 25, p. 89, (1999).

* cited by examiner

AGENT FOR INCREASING GRANULOCYTE MACROPHAGE COLONY STIMULATING FACTOR

TECHNICAL FIELD

The present invention relates to an agent for increasing a granulocyte-macrophage colony stimulating factor characterized by comprising four kinds of crude drugs, i.e. *Cucurbita moschata, Carthamus tinctorius, Plantago asiatica* and *Lonicera japonica*.

BACKGROUND ART

A granulocyte-macrophage colony stimulating factor (GM-CSF) has an action for stimulating the proliferation and differentiation of granulocyte progenitor and is a glycoprotein having a molecular weight of 22,000, which produces neutrophils, acidocytes and monocytes within an organism.

As the diseases associated with a blood state of low GM-CSF level, there are mentioned neutropenia, aplastic anemia, osteomyelodysplasia syndrome, or the like, and GM-CSF is in use for treatment of these diseases (e.g. Hideaki Mizoguchi, GM-CSF, Cytokine Therapy: Approach from Basis and Pathema, Nankodo Co., Ltd., Tokyo, p. 39-45, 1993, ISBN: 4524233628). Also, it is shown that two cytokines of granulocyte colony stimulating factor (G-CSF) and GM-CSF stimulate the proliferation of granulocyte progenitor fraction and shorten the duration of decrease of neutrophil, and they are in use as first-line drugs for leucopenia and granulopenia (e.g. Merck Manual 16th Edition, p. 1240, 1994).

Tumor necrosis factor (TNF) was reported for the first time as a factor which kills tumor cells in vitro. Thereafter, lymphotoxin-α (LT-α) and lymphotoxin-β (LT-β) were identified as factors having similar bioactivities. TNF is a general term of molecules having a tumor cell-killing effect, and there are known three kinds, i.e. TNF-α, TNF-β (LT-α) and LT-β. TNF bonds with receptors present in almost all cells within an organism and thereby exhibits extensive actions (e.g. Tsutomu Takeuchi, Separate Volume: Progress of Medical Science, Immunodeficiency, Ishiyakushuppan Co., Ltd., Anti-TNF α Therapy, p. 538-542, 2002).

TNF is a multifunctional cytokine which exhibits different activities to various kinds of cells in vitro tests. As the diseases caused by an increase in TNF-α, there are known rheumatoid arthritis (RA), Crohn's disease and inflammatory bowel disease (IBD). For example, it is reported that, in patients of rheumatoid arthritis, TNF-α reaches 15.0±9.2 pg/ml (e.g. Masahiro Yamamura, Clinical Analysis and Treatment of Anemia in Patients of Rheumatoid Arthritis, Report for 6th, Incentive Award of the Society of Certifying Specialist in Internal Medicine, 1998) and, in Crohn's disease, the average TNF-α of four patients in inactive period is 11.98 pg/ml and the average TNF-α of four patients in active period is 404.76 pg/ml (e.g. Naoki Watanabe, Development of Highly Sensitive Assay for Detection of Intravital Trace Materials and Its Clinical Application, Lab. Clin. Pract., 20(2), p. 110-114, 2002).

RA is a cryptogenic chronic inflammatory disease which appears mainly at synovial membrane of joint. It was made clear that, in articular cavity, inflammatory cytokines such as TNF-α, IL-1, IL-6 and the like are produced in excess and participate in formation of joint lesion such as lymphocytic infiltration, synovial hyperplasia and destruction of cartilage tissue by osteoclast. Arthritis was caused in a model animal in which was high expression of TNF-α and, when the TNF-α was neutralized with an anti-TNF-α monoclonal antibody, striking improvement of the arthritis was seen. In association therewith, IL-1 and IL-6 concentrations decreased. Based on this, it has considered that TNF-α has a close connection with excessive production of the above inflammatory cytokines and plays a central role in formation of RA lesion at an upstream of cytokine cascade (e.g. Tsutomu Takeuchi, Appendix: Progress of Medical Science, Immunodeficiency, Anti-TNF α Therapy, Ishiyakushuppan Co., Ltd., p. 538-542, 2002). The anti-TNF-α monoclonal antibody was approved as a remedy for rheumatoid already in 1999 in U.S.A.

Crohn's disease is a disease in which inflammation of unknown etiology persists mainly in the small intestine and the large intestine and induces the beginning of ulcer, the sequential expression of stenosis, abscess and fistula in the intestinal tract. Crohn's disease is often difficult to differentiate from ulcerative colitis and, together with ulcerative colitis, is generally called as Inflammatory Bowel Disease (IBD). In treatment of Crohn's disease, it is important to effectively control the persisting inflammation of intestinal tract. Substances associated with inflammation include several tens of kinds and, of them, TNF-α has been clarified to have a central role. A large amount of TNF-α is produced and present when the inflammatory intestinal duct of a patient of Crohn's disease is examined. This large amount of TNF-α cause further inflammation; therefore, in order to break out of the vicious cycle of inflammation, counteractive to the effect of TNF-α have been developed. Also, a thalidomide therapy has been applied to refractory Crohn's disease and the effectiveness of thalidomide to some cases was proven (e.g. Ehrenpreis E D, Thalidomide therapy for patients with refractory Crohn's disease: An open-label trial, Gastroenterology, 117, p. 1271-1277, 1999). Also, a chimeric monoclonal anti-TNF antibody (Infliximab, manufactured by Centocor, Inc., U.S.A.) was proven as a first remedy by biotechnology in the field of gastroenterological disease, in 1999 in U.S.A. It is reported that the treatment using the remedy suppresses the inflammation of Crohn's ileocolitis significantly (e.g. Baert FL. Tumor necrosis factor α-antibody (Infliximab) therapy profoundly down-regulates the inflammation in Crohn's ileocolitis. Gastroenterology, 116, p. 22-28, 1999). In Japan, the above antibody was approved as a remedy for Crohn's disease in January, 2002.

Meanwhile, as to *Cucurbita moschata, Carthamus tinctorius, Plantago asiatica* and *Lonicera japonica*, respective efficacies are reported as follows. For example, it is disclosed that addition, to a feed, of at least one kind of *Cucurbita moschata, Plantago asiatica* and *Lonicera japonica* (particularly, a crude drug comprising these three crude drugs) can prevent, in particular, natural infection of parasites, bacteria and viruses and can achieve higher biophylaxis ability and improved meat and egg qualities. Further, it has been disclosed that a feed comprising four kinds of crude drugs, i.e. *Cucurbita moschata, Plantago asiatica, Lonicera japonica* and *Carthamus tinctorius* improves the health conditions, survival rates, quality of egg, and has anti-leucocytozoonosis effect in layers, and anti-New-Castle-disease effect and effects of the decreased numbers of enteric *Coccidium* and *Staphylococcus* in the intestine of quails (e.g. U.S. Pat. No. 5,882,672).

A method for producing an interferon inducer from the plants of the genus Cucurbitaceae such as pumpkin has been disclosed (e.g. U.S. Pat. No. 4,421,746). The antiviral activity and anti-tumor activity of interferon inducers extracted from the flowers of *Carthamus tinctorius* has been disclosed (e.g. U.S. Pat. No. 4,456,597). It has also been disclosed that interferon inducers may be extracted from the flowers of *Lonicera japonica*, seeds of *Plantago asiatica*, and the like, and that the extracted interferon inducers are useful for prevention and curative treatments of viral infections in humans and animals (e.g. U.S. Pat. No. 4,469,685). A macrophage activator comprising two crude drugs of *Cucurbita moschata* and *Carthamus tinctorius* has also been disclosed (e.g. Japanese Patent Laid-open No. 116498/1999). A neutrophil activator comprising four crude drugs of *Cucurbita moschata, Carthamus tinctorius, Plantago asiatica* and *Lonicera japonica* has also been disclosed (e.g. Japanese Patent Laid-open No. 281584/2000).

However, while these documents disclose the interferon inducing effects, macrophage activating effects, neutrophil activating effects, the inhibitory effects of IgE anti-body production, and the like of the crude drugs used as active components in the present invention, none of the references disclose or suggest the increasing action for GM-CSF concentration in blood or on the proliferating action for granulocyte or macrophage.

The aim of the present invention is to provide a GM-CSF increasing agent comprising, as active components, crude drugs, specifically, *Cucurbita moschata, Carthamus tinctorius, Plantago asiatica* and *Lonicera japonica*.

DISCLOSURE OF THE INVENTION

As a result extensive studies on crude drugs obtained from plants, the present inventors have discovered that by administering a composition comprising *Cucurbita moschata, Carthamus tinctorius, Plantago asiatica* and *Lonicera japonica*, the blood GM-CSF concentration increased significantly for a period of six months.

Hence, the present invention relates to (1) a GM-CSF increasing agent comprising, as active components, *Cucurbita moschata, Carthamus tinctorius, Plantago asiatica* and *Lonicera japonica*; (2) a GM-CSF increasing agent according to (1), which is a health food or functional food for amelioration or alleviation of the nose or symptoms of neutropenia; (3) a GM-CSF increasing agent according to (1), which is a health food or functional food for amelioration or alleviation of the nose or symptoms of aplastic anemia; and (4) a GM-CSF increasing agent according to (1), which is a health food or functional food for amelioration or alleviation of the nose or symptoms of osteomyelodysplasia.

Incidentally, the present invention relates to a composition which can be used together with conventional remedy for the above-mentioned diseases, etc.

BEST MODE FOR CARRYING OUT THE INVENTION

The present invention will now be described in more detail below.

First, description is made on the crude drugs used in the present invention.

*Cucurbita moschata* are seeds originate from a plant belonging to the genus Cucurbitaceae (Japanese name: Nihon-kabocha; *Cucurbita moschata* Duch). In addition, to these seeds, seeds of related plants capable of achieving the object of the present invention may be used. Although raw seeds may be used, dry seeds are preferred because of their superior storability when used as a medicine or health food. A part of seed hull may be used. *Cucurbita moschata* contain components such as cucurbitin, protein, vitamins A, $B_1$, $B_2$ and C, and further contain carotene, and the like.

*Carthamus tinctorius* is the dried tubular flower of a plant belonging to the genus Compositae (known as safflower flower; *Carthamus tinctorius* L.). It contains components such as carthamin, safflor yellow, lignan and sterol.

*Plantago asiatica* belongs to the genus Plantaginacea (known as Plantain; *Plantago asiatica* L.) and its matured seeds or the entire plant may be used. It contains components such as polysaccharides, plantenolic acid, succinic acid, adenine, aucubin, plantaginin, and vitamins A and $B_1$.

*Lonicera japonica* belongs to the genus Gramineae (known as honeysuckle; *Lonicera japonica* Thunb.) and its flower, bud, leaf, stem or the entire plant may be used. It contains components such as wax-like material, inositol, tannin, saponin, and lonicerin.

In the present invention, a crude powder of these crude drugs or an extract of these crude drugs obtained using water or an organic solvent may be used. Specifically, the crude drugs are used in the form of a crude powder, solvent preparation, powder preparation, compression, infusion, or the like.

The crude powder of these crude drugs can be obtained by chopping or powdering the raw plant, the material obtained by drying in the shade, or the dried material. As the organic solvent, ethanol, acetone, and the like can be used. A mixture of these organic solvents with water or a mixture of two or more organic solvents may be used. The extract can be obtained by adding the solvent in an amount of several times the crude drugs and extracting or infusing the mixture at ordinary temperature or with heating. Each of the crude drugs may be extracted separately and then mixed, or a mixture of the crude powders of several crude drugs prepared beforehand may be extracted.

The above-mentioned crude powder or extract obtained by extraction with water or an organic solvent of the crude drug may be used as it is, or prepared into various forms according to per se known methods, for use as a medical composition, health food or functional food (supplement).

The medical composition or functional food (supplement) may be provided in the form of tablets, powder, granules, capsules, pills, or syrup for oral administration by a conventional method of preparation. During preparation, as necessary, excipients, binders, disintegrators, lubricants, buffering agents, sweeteners, stabilizers, and the like may be used. In addition, at least one inert diluent such as lactose, mannitol, glucose, hydroxypropyl cellulose, finely crystallized cellulose, starch, polyvinyl pyrrolidone, and magnesium metasilicate aluminate may be used. In addition to the inert diluents, the composition may contain additives, for example, lubricants such as magnesium stearate, starch and talc, disintegrators such as calcium cellulose glycolate, stabilizers such as lactose, and solubilizer adjuvants such as glutamic acid and aspartic acid in accordance with conventional method. Tablets or pills may be coated with a sugar or a film of a substance soluble in the stomach or intestines such as sucrose, gelatin, agar, pectin, hydroxypropyl cellulose, and hydroxypropyl methyl cellulose phthalate, as necessary.

Other additives may be added to the composition of the present invention to the extent that the effect of the crude drug active component is not adversely affected. Such additives include water-soluble vitamins such as caffeine, vitamin $B_1$, vitamin $B_2$, vitamin $B_6$, vitamin $B_{12}$, vitamin C, biotin, carnitine, pantothenic acid, nicotinic acid, and derivatives thereof, fat-soluble vitamins such as vitamin A, vitamin E, and derivatives thereof, amino acids such as taurine and arginine, oriental herbs such as *perilla*, licorice root, *ginkgo*, dandelion, *chrysanthemum*, ginseng, and cinnamon, western herbs such as saw palmetto, St. John's wort, *echinacea*, aniseed, annual chamomile, rosemary, mint, *Eucalyptus*, lavender, rose, *hibiscus, aloe* and the like.

In addition, in accordance with the method of use, other active components as oligosaccharides such as lactulose or commercial lactic acid bacteria such as bifidus may also be used.

Liquid compositions for oral administration include pharmaceutically accepted emulsifier, solvents, suspending agents, syrup, and elixirs, and contain a commonly used inert diluent such as purified water and ethanol. In addition to the inert diluent, the composition may also contain moisturizers, adjuvants such as suspending agents, sweeteners, flavorants, fragrances, and antiseptics.

In the case of a health food, the composition can be provided in the forms of a beverage or a confection such as a jelly, biscuit, cookie, or candy.

The composition of the present invention contains crude drugs of *Cucurbita moschata, Carthamus tinctorius, Plantago asiatica* and *Lonicera japonica* as active components. Preferably, the composition contains, in particular, *Cucurbita moschata* in range from 20 to 60% by weight, *Carthamus tinctorius* in range from 10 to 40% by weight, and each of the other crude drugs in range from 5 to 70% by weight.

The amount of the active components to be administered can be appropriately determined based on the age, sex, and the like of patient. Usually, in the case of an adult weighing 60 kg, the crude drugs are administered orally in a combined amount of 0.5-5 g and preferably 1-3 g on a daily basis.

Also, the present invention can be applied not only to humans but also to livestock, poultry and companion animals such as a dog, cat, and the like, as a remedy or as a health food or functional food for amelioration or remission of symptoms.

EXAMPLES

The present invention will now be described in more detail below by way of Production examples and Examples, which should not be construed as limiting the present invention.

Production Example 1

The crude powders of the following crude drugs as components were compounded. The resulting compound was extracted with ten times the amount of hot water a temperature of at 95±5° C. for 30 minutes. The extract was filtered and then concentrated, followed by addition of excipients such as reduced maltose, lactose or starch and fragrance, or the like. The resulting material was granulated to produce fine granules. The components (mixed ratios) in each fine granules were as follows.

*Cucurbita moschata* (50%), *Carthamus tinctorius* (20%), *Plantago asiatica*: (15%), *Lonicera japonica* (15%)

Production Example 2

5.0 g of *Cucurbita moschata*, 3.0 g of *Carthamus tinctorius*, 1.0 g of *Plantago asiatica* and 3.0 g of *Lonicera japonica*, 67 g of lactose and 16 g of starch were mixed uniformly in a mixer. The resulting mixture was kneaded using a solution obtained by dissolving 2 g of hydroxypropyl cellulose and 5 g of capric acid triglyceride. The kneaded material was granulated using a basket type granulator (screen diameter: 1 mm); the granules were passed through a 14-mesh sieve and dried to obtain columnar granules. The granules were uniformly mixed with mannitol, hydroxypropyl cellulose, magnesium metasilicate aluminate, aspartame and a fragrance to obtain 12 chartulae of granules (Japanese Patent Laid-open No. 231584/2000).

In the following, compositions with various component ratios (% by weight) can be prepared in the same manner as that of Production Example 1.

TABLE 1

| Formulation Example | Cucurbita moschata seeds | Carthamus tinctorius flowers | Plantago asiatica seeds | Lonicera japonica flowers |
|---|---|---|---|---|
| 1  | 60 | 20 | 10 | 10 |
| 2  | 50 | 20 | 15 | 15 |
| 3  | 50 | 10 | 25 | 15 |
| 4  | 45 | 20 | 30 | 5  |
| 5  | 42 | 25 | 8  | 25 |
| 6  | 40 | 30 | 20 | 10 |
| 7  | 25 | 10 | 40 | 25 |
| 8  | 25 | 15 | 38 | 22 |
| 9  | 25 | 25 | 25 | 25 |
| 10 | 25 | 25 | 5  | 45 |
| 11 | 20 | 40 | 20 | 20 |
| 12 | 20 | 10 | 60 | 10 |
| 13 | 25 | 25 | 25 | 25 |

Production Example 3

Crude powders of crude drugs of *Cucurbita moschata, Carthamus tinctorius, Plantago asiatica*, and *Lonicera japonica* was mixed and the resulting mixture was extracted with 10 times the amount of hot water at a temperature of 95±5° C. for 30 minutes. The extract was filtered and concentrated, followed by addition of excipients such as reducing maltose, lactose, starch, and the like, and fragrance. The resulting material was granulated to produce fine granules [InterPunch (registered brand, manufactured by Sanwell Co., Ltd.)]. The composition thereof is shown in.

TABLE 2

| Nutrient composition per two sachets (1.5 g × 2) of InterPunch | |
|---|---|
| Calorie | 11.5 Kcal |
| Protein | 0.042 g |
| Fat | 0.003 g |
| Sugar | 2.823 g |
| Dietary fiber | 0.03 g |
| Sodium | 0.444 mg |
| Lactulose | 400 mg |
| *Cucurbita moschata* seeds | Mixed extract |
| *Plantago asiatica* seeds | equivalent to 1000 mg |
| *Carthamus tinctorius* flowers | of raw material |
| *Lonicera japonica* flowers | |
| Bifidus | 40 mg |

Example 1

Clinical Test for Measurement of GM-CSF Amount

The composition obtained in Production Example 3 was administered to 32 volunteers for a period of six months in an amount of 6 g on a daily basis, and the blood GM-CSF concentration was measured by an enzyme immunoassay to evaluate the efficacy of the composition.

Test Result:

Comparison of GM-CSF concentrations in blood before administration and after six month administration indicates that there was conducted a significant difference test (Mann-Whitney U-test) based on the GM-CFS concentration values before administration and after six month administration. As the result, there was a significant increase ($P<0.05$).

Thus, the composition of the present invention (Production Example 3) was proven to be a GM-CSF increasing agent.

Further, during the test period of ingestion, there was no harmful phenomenon based on subjective symptoms and objective observations by doctor, and the safety of the composition was confirmed.

Example 2

Clinical Test for Measurement of Blood TNF-α Concentration

The composition obtained in Production Example 3 was administered to 25 volunteers (aged from 48 to 66) for a period of three months in an amount of 6 g on a daily basis, and the blood TNF-α concentration was measured by an enzyme immunoassay to evaluate the efficacy of the composition.

Test Result:

The TNF-α of 10 volunteers was 4.0±2.9 pg/ml (a range from 1.5 to 9.5 pg/ml) before the administration and, after three month administration, decreased to 2.40±2.0 pg/ml. There was conducted a significant difference test (t-test) based on the TNF-α values before administration and after three month administration. As a result, there was a significant decrease ($P<0.05$).

Meanwhile, the TNF-α of remaining 15 volunteers was 1.1±0.3 pg/ml (a range from 0.3 to 1.4 pg/ml) before the administration and, after three month administration, was 1.0±0.3 pg/ml (no change).

Ordinary immunostimulants or immunosuppressants have either a TNF-α increasing action or a TNF-α decreasing action. However, the composition of Production Example 3 was found to have an extremely specific function of decreasing a high TNF-α level depending upon the pathema of patient and not altering a low TNF-α level.

Therefore, the composition of Production Example 3 has a possibility of decreasing an undesirably high TNF-α level to an appropriate level.

Further, during the test period of ingestion, there was no harmful phenomenon based on subjective symptoms and objective observations by doctor, and the safety of the composition was confirmed.

Example 3

Respective crude powders of *Cucurbita moschata*, *Carthamus tinctorius*, *Plantago asiatica* and *Lonicera japonica*, a crude powder of a compound of these 4 kinds of plants (compounding ratio: shown in Production Example 1), and licorice (its components such as glycyrrhizin and the like are known to have an action on the immune system) were extracted with ten times the amount of hot water at a temperature of 95±5° C. for 30 minutes. Each extract was filtered and then concentrated, followed by a granulation step to produce various kinds of fine granules (various hot-water extracts). Using these extracts, there were measured human TNF activities in human monocyte/macrophage cell, THP-1, by ELISA. The above hot-water extracts were dissolved in water (300 μg/ml) and tested as groups 1 to 6 (group 1: an extract of Production Example 1, group 2: an extract of *Cucurbita moschata*, group 3: an extract of *Carthamus tinctorius*, group 4: an extract of *Plantago asiatica*; group 5: an extract of *Lonicera japonica*, group 6: an extract of licorice). Since the extracts of groups 1 to 6 were not subjected to a lipopolysaccharide-removing step, there was used, as a positive control, LPS (lipopolysaccharide) (SIGMA-ALDRICH: LIPOSACCHARIDE L-2880); and LPS 100 μg/ml, 10 μg/ml, 1 μg/ml and 0.1 μg/ml were tested as groups 7 to 10.

In the results, the groups 7 to 10 as LPS group dose-dependently produced TNF-α in amount of 22.4 pg/ml, 8.5 pg/ml, 1.7 pg/ml and 0.0 pg/ml, respectively. In the single-plant extract groups 2 to 6, the amount of TNF-α produced were 2.1 pg/ml, 6.1 pg/ml, 2.2 pg/ml, 0.6 pg/ml and 0.0 pg/ml, respectively.

Meanwhile, the extract of the present invention product showed a high TNF-α level of 34.2 pg/ml. Licorice produced no TNF-α.

The four kinds of plants constituting the composition of the present invention have each an activity and, of the four kinds, *Carthamus tinctorius* gave the highest TNF-α level of 6.1 pg/ml. If it is assumed that the TNF-α production by each plant extract was caused only by the LPS contained in each plant extract, it follows that *Carthamus tinctorius* contained LPS corresponding to about 7.2 pg/ml of TNF-α. However, the composition of the present invention (containing the extracts of 4 kinds of plants) produced TNF-α in an amount of 5.6 times that of *Carthamus tinctorius* alone. Therefore, it was found that mixing of four kinds of plants increased the amount of TNF-α produced by a synergistic effect. Thus, it was confirmed that the extract containing 300 μg/ml of the composition of the present invention exhibited a TNF-α increasing action comparable to about 150 μg/ml of LPS.

Example 4

Test on GM-CSF Increasing Action

A extract of Production Example 1 was used as a substance to be tested. The extract was orally administered to 10 laboratory rats (SD strain, SPF grade) at a dose of 1,000 mg/60 kg. After the lapse of given time after administration, blood was collected from the animals. Macrophages were separated from the blood and subjected to incubation. The incubated macrophages were sensitized with the MACH extract. After the lapse of given time after the sensitization, the GM-CSF concentration in macrophages was measured. As a result, there was an increase (very small) tendency of GM-CSF concentration, as compared with a control. It is considered that the above result complements the increase of GM-CSF in human after long-term administration.

INDUSTRIAL APPLICABILITY

The present invention has an action of increasing the amount of GM-CSF blood and accordingly can be expected for the treatment of diseases associated with low GM-CSF amount, for example, neutropenia and aplastic anemia.

Further, the present invention has a possibility of being used as a supplement, health food, or the like. for GM-CSF increase, which can avoid undesirable symptoms seen upon administration of GM-CSF [fever (e.g. Akio Urabe, Blood Disease and Cytokine Therapy, Cytokine Therapy Approach from Start and Pathema, Nankodo Co., Ltd., Tokyo, p. 184 to 194, 1993), minor flu-like syndrome (myalgia, chill, pain of bone, diarrhea, nausea, malaise and headache), erythematous rash caused by subcutaneous injection of GM-CSF, and dyspnea caused by hypotension and hypoxia seen sometimes at the initial administration of GM-CSF (e.g. Cytokine Reference A compendium of cytokines and other mediators of host defense, GM-CSF, Academic Press, p. 899-910, 2001)].

Further, the composition of the present invention has been confirmed to have an action of decreasing a high TNF-α level and, for incubated cells, an action of increasing TNF-α when a compound of four kinds of plants is used; therefore, it is considered that the present composition can be expected as an immunomodulator (an immunomodifier) rather than as an immunostimulant (which stimulates and activates the immune system) or an immunosuppressant (which suppresses the immune system). The present composition can be expected, for example, as a nutritional supplementary food, health food, or the like. for prevention or prognosis of Inflammatory Bowel Diseases (IBD) or Crohn's disease and the like.

The invention claimed is:

1. A method of treating neutropenia comprising administering an effective amount of a composition comprising, as active components, from 20 to 60% by weight *Cucurbita moschata*, from 10 to 40% by weight *Carthamus tinctorius*, from 5 to 70% by weight *Plantago asiatica*, and from 5 to 70% by weight *Lonicera japonica* to a patient suffering from neutropenia.

2. A method of treating aplastic anemia, comprising administering an effective amount of a composition comprising, as active components, from 20 to 60% by weight *Cucurbita moschata*, from 10 to 40% by weight *Carthamus tinctorius*, from 5 to 70% by weight *Plantago asiatica*, and from 5 to 70% by weight *Lonicera japonica* to a patient suffering from aplastic anemia.

* * * * *